US012749582B2

(12) United States Patent
Stancombe et al.

(10) Patent No.: US 12,749,582 B2
(45) Date of Patent: Sep. 29, 2026

(54) APPARATUS AND PROCESS FOR MEDICAL SENSING

(71) Applicant: EMvision Medical Devices Ltd, Brisbane (AU)

(72) Inventors: Anthony Stancombe, Brisbane (AU); Konstanty Bialkowski, Brisbane (AU); David Cook, Brisbane (AU); Amin Abbosh, Brisbane (AU)

(73) Assignee: EMvision Medical Devices Ltd, Brisbane (AU)

( * ) Notice: Subject to any disclaimer, the term of this patent is extended or adjusted under 35 U.S.C. 154(b) by 189 days.

(21) Appl. No.: 18/555,500

(22) PCT Filed: Apr. 13, 2022

(86) PCT No.: PCT/AU2022/050331

§ 371 (c)(1),
(2) Date: Oct. 13, 2023

(87) PCT Pub. No.: WO2022/217311

PCT Pub. Date: Oct. 20, 2022

(65) Prior Publication Data

US 2024/0194349 A1 Jun. 13, 2024

(30) Foreign Application Priority Data

Apr. 13, 2021 (AU) ................................ 2021901079

(51) Int. Cl.
*G16H 50/20* (2018.01)
*A61B 5/00* (2006.01)

(52) U.S. Cl.
CPC ........... *G16H 50/20* (2018.01); *A61B 5/4064* (2013.01)

(58) Field of Classification Search
CPC .............................. G16H 50/20; A61B 5/4064
See application file for complete search history.

(56) References Cited

U.S. PATENT DOCUMENTS 10,660,531 B1 * 5/2020 Libove .................. A61B 5/369
10,709,345 B1 7/2020 Michaeli et al.
(Continued)

FOREIGN PATENT DOCUMENTS

WO WO 2020/047599 A1 3/2020
WO WO 2021/026592 A1 2/2021

OTHER PUBLICATIONS

Brankovic et al., "Unsupervised Algorithm for Brain Anomalies Localization in Electromagnetic Imaging," IEEE Transactions on Computational Imaging, Dec. 4, 2020, vol. 6, pp. 1595-1606.
(Continued)

*Primary Examiner* — Hugh Maupin
(74) *Attorney, Agent, or Firm* — KNOBBE, MARTENS, OLSON & BEAR, LLP

(57) ABSTRACT

A computer-implemented process for medical sensing, the process including the steps of: accessing scattering data representing successive sets of measurements of electromagnetic wave scattering by internal features of a body part of a living subject, each said measurement representing scattering of electromagnetic waves emitted by a corresponding antenna of an array of antennas disposed about the body part as measured by a corresponding antenna of the array of antennas at a corresponding time, wherein the successive sets of measurements are temporally spaced apart; processing each of the measurements to generate corresponding spectral data representing intensities measured by the corresponding antenna at the corresponding time as a function of frequency; and processing the spectral data of each antenna for successive times to generate corresponding pulsatility data representing successive pulsations within a corresponding spatially localized region within the body part.

14 Claims, 7 Drawing Sheets

(56) References Cited

U.S. PATENT DOCUMENTS

| | | | | |
|---|---|---|---|---|
| 11,089,964 | B1 * | 8/2021 | Libove | A61B 5/0042 |
| 12,002,584 | B2 * | 6/2024 | Alon | G16H 10/60 |
| 2003/0018244 | A1 * | 1/2003 | Haddad | A61B 5/0507 600/371 |
| 2007/0276270 | A1 * | 11/2007 | Tran | A61B 5/0022 600/508 |
| 2008/0252293 | A1 * | 10/2008 | Lagae | H04B 1/7163 324/318 |
| 2014/0163385 | A1 * | 6/2014 | Kelleher | A61B 8/4416 600/407 |
| 2014/0222126 | A1 * | 8/2014 | Xiao | A61N 5/02 607/139 |
| 2014/0288412 | A1 * | 9/2014 | Schwartz | A61B 5/1114 600/407 |
| 2016/0139222 | A1 | 5/2016 | Frydman et al. | |
| 2016/0278653 | A1 * | 9/2016 | Clark | A61B 5/4094 |
| 2017/0074957 | A1 | 3/2017 | Idiyatullin et al. | |
| 2017/0143231 | A1 | 5/2017 | Østberg et al. | |
| 2019/0069876 | A1 | 3/2019 | Michaeli et al. | |
| 2019/0282191 | A1 | 9/2019 | Williams | |
| 2019/0313937 | A1 * | 10/2019 | Fhager | A61B 5/72 |
| 2021/0335493 | A1 * | 10/2021 | Alon | A61B 5/0507 |

OTHER PUBLICATIONS

Trakic et al., "Expedited Stroke Imaging With Electromagnetic Polar Sensitivity Encoding," IEEE Transactions on Antennas and Propagation, Dec. 2020, vol. 68, No. 12, pp. 8072-8081.

Extended European Search Report Issued in European Patent Application No. 22787160.5, dated Feb. 7, 2025, in 11 pages.

International Search Report dated Jun. 6, 2022, for International Patent Application No. PCT/AU2022/050331, 5 pages.

* cited by examiner

APPARATUS AND PROCESS FOR MEDICAL SENSING

TECHNICAL FIELD

The present invention relates to medical sensing or imaging, and in particular to an apparatus and process for medical sensing.

BACKGROUND

The reference in this specification to any prior publication (or information derived from it), or to any matter which is known, is not, and should not be taken as an acknowledgment or admission or any form of suggestion that that prior publication (or information derived from it) or known matter forms part of the common general knowledge in a field of endeavour to which this specification relates.

Whilst magnetic resonance imaging (MRI) and computed tomography (CT) are gold standard medical imaging modalities, they are very expensive, limited in number for a given community, bulky and non-portable for emergency situations, and take a very long time (typically up to about 40 min) to prepare and scan a body part of a patient. Accordingly, electromagnetic based imaging, localization and classification of stroke and other pathologies has been widely studied in the literature as a much more affordable, readily available and portable imaging alternative. Low-power electromagnetic based imaging (at frequencies from 100 MHz and typically up to no more than 4 GHz) is of particular interest because the shorter wavelength electromagnetic fields can penetrate further into the human head and produce images with higher spatial resolution than electromagnetic fields with frequencies below 100 MHz.

Research studies are performed utilizing antenna arrays, wherein each antenna has a corresponding dedicated and independent electronic transmit-receive channel to enable the collection of an entire matrix of measured scattering parameters, typically but not always being "S-parameters" or "Z-parameters", these being standard forms known to those skilled in the art. For example, for each frequency point in a spectrum of frequencies, the $S_{ii}$ and $S_{ij}$-parameters can be directly collected by a vector network analyzer and stored as a 2-dimensional N×N matrix, where N is the number of channels (and the number of antennas in the array). In the remainder of this specification, S-parameter measurements are used as representative examples of scattering parameters, although it should be understood that other types of electromagnetic scattering measurements known to those skilled in the art, such as Z-parameters for example, can be used instead of or in addition to S-parameters.

The antennas can be wide and varied in configuration and style, for instance often taking the form of dielectrically loaded waveguides or patch antennas. The size of the antennas determines both the number of antennas that can be fitted around the head or other body part of a patient, as well as the frequency bandwidth over which the antennas are able to operate. For example in the case of the human head imaging, typically the antennas are arranged circumferentially around the head, with each pointing towards the head. Normally, a coupling medium is inserted between the antenna aperture and the head surface in order to reduce the impedance mismatch and power reflection.

In the case of stroke disease, strokes typically occur in one of two types: (i) hemorrhagic or (ii) ischemic. A hemorrhagic stroke is a type of stroke wherein a blood vessel has ruptured, causing uncontrollable bleeding into normal tissue regions, often resulting in substantial intracranial pressure, and leading to partial/complete disability, coma, or death. Similarly dangerous is the ischemic stroke, wherein a small (blood) clot has blocked blood flow to a certain part of the brain. This type of stroke is typically below the spatial resolution of microwave imaging, and is usually not immediately visible and differentiable from normal tissue, even on MRI and CT scans. However, the loss of a fresh blood supply means that the surrounding tissue will have a lower water content and can cause tissue death. The electromagnetic dielectric properties (electrical conductivity and relative permittivity) of an ischemic stroke at this stage are known to be approximately 5-20% lower than the head-average dielectric properties of healthy tissue, and consequently provide a contrast with respect to the neighboring healthy tissue. Additionally, over several hours or days, as a water-based oedema forms around the clot occlusion, an ischemic stroke provides dielectric properties higher than the hemorrhagic stroke. Each of these states and classes of strokes provides different magnitude and phase information, and can be detected using microwave imaging technology.

To image such diseases using electromagnetic medical imaging, tomographic imaging methods are used, relying on electromagnetic field solvers based on Maxwell's field equations or variants of the same implemented on a high-speed computer. These electromagnetic field solvers are often referred to in the art as 'forward' or 'inverse' solvers, and are used in conjunction with the S-parameter measurements as part of the objective function to iteratively optimize a calculated electromagnetic field so that it matches that of the real-world case. There are vast numbers of such algorithms, which are often based on local/global integral or differential tomographic models, often containing Born iterative solvers. Normally the outputs of such optimizations are spatial maps of electrical conductivity and relative permittivity of tissue, often (roughly) indicating the spatial distribution of dielectric properties of the target (i.e., abnormal) tissue, which may or may not be easily visible and differentiated from the surrounding dielectric distribution of normal tissue. In addition, tomographic methods need to solve for orders of magnitude larger number of unknowns than the number of known measurements (e.g., such as for example 10,000 unknowns in a 100×100 2D tomographic image, whereas the number of measurements is for example only 169 given an array of 14 antennas).

It is desired to provide an apparatus and computer-implemented process for medical sensing that overcome or alleviate one or more difficulties of the prior art, or to at least provide a useful alternative.

SUMMARY

In accordance with some embodiments of the present invention, there is provided a computer-implemented process for medical sensing, the process including the steps of:

- accessing scattering data representing successive sets of measurements of electromagnetic wave scattering by internal features of a body part of a living subject, each said measurement representing scattering of electromagnetic waves emitted by a corresponding antenna of an array of antennas disposed about the body part as measured by a corresponding antenna of the array of antennas at a corresponding time, wherein the successive sets of measurements are temporally spaced apart;
- processing each of the measurements to generate corresponding spectral data representing intensities measured by the corresponding antenna at the corresponding time as a function of frequency; and processing the spectral data of each antenna for successive times to generate corresponding pulsatility data representing pulsations within a corresponding spatially localized region within the body part.

In some embodiments, the temporal spacing between successive measurements of each antenna is about 0.03 seconds or less.

In some embodiments, the body part is the subject's head, and the pulsatility data represents pulsations within a corresponding spatially localized region within the subject's brain.

In some embodiments, the process includes processing the pulsatility data of each antenna to diagnose a brain condition of the subject. The brain condition may be a brain condition selected from: haemorrhagic stroke, ischemic stroke, traumatic brain injury, and hydrocephalus.

In some embodiments, said processing includes processing time domain signals representing the measurements of electromagnetic wave scattering to select a portion of each time domain signal corresponding to scattering within the body part, and processing the selected portions of the time domain signals to generate the spectral data.

In accordance with some embodiments of the present invention, there is provided an apparatus for medical sensing, the apparatus including at least one processor configured to execute any one of the above processes.

In accordance with some embodiments of the present invention, there is provided a computer-readable storage medium having stored thereon executable instructions that, when executed by at least one processor of a data processing apparatus, cause the apparatus to execute any one of the above processes.

In accordance with some embodiments of the present invention, there is provided an apparatus for medical sensing, including:

an acquisition component configured to access scattering data representing successive sets of measurements of electromagnetic wave scattering by internal features of a body part of a living subject, each said measurement representing scattering of electromagnetic waves emitted by a corresponding antenna of an array of antennas disposed about the body part as measured by a corresponding antenna of the array of antennas at a corresponding time, wherein the successive sets of measurements are temporally spaced apart;

a spectral generation component configured to process each of the measurements to generate corresponding spectral data representing intensities measured by the corresponding antenna at the corresponding time as a function of frequency; and a pulsatility generation component configured to process the spectral data of each antenna for successive times to generate corresponding pulsatility data representing successive pulsations within a corresponding spatially localized region within the body part.

In some embodiments, the temporal spacing between successive measurements of each antenna is about 0.03 seconds or less.

In some embodiments, the body part is the subject's head, and the pulsatility data represents pulsations within a corresponding spatially localized region within the subject's brain.

In some embodiments, the apparatus includes a diagnosis component configured to process the pulsatility data of each antenna to diagnose a brain condition of the subject. The brain condition may be a brain condition selected from: haemorrhagic stroke, ischemic stroke, traumatic brain injury, and hydrocephalus.

In some embodiments, the spectral generation component is configured to process time domain signals representing the measurements of electromagnetic wave scattering to select a portion of each time domain signal corresponding to scattering within the body part, and to process the selected portions of the time domain signals to generate the spectral data.

BRIEF DESCRIPTION OF THE DRAWINGS

Some embodiments of the present invention are hereinafter described, by way of example only, with reference to the accompanying drawings, wherein:

FIG. 3 (*c*) illustrates the pulsatility signals generated from the spectral data of FIG. 3 (*b*);

DETAILED DESCRIPTION

Figure 1:
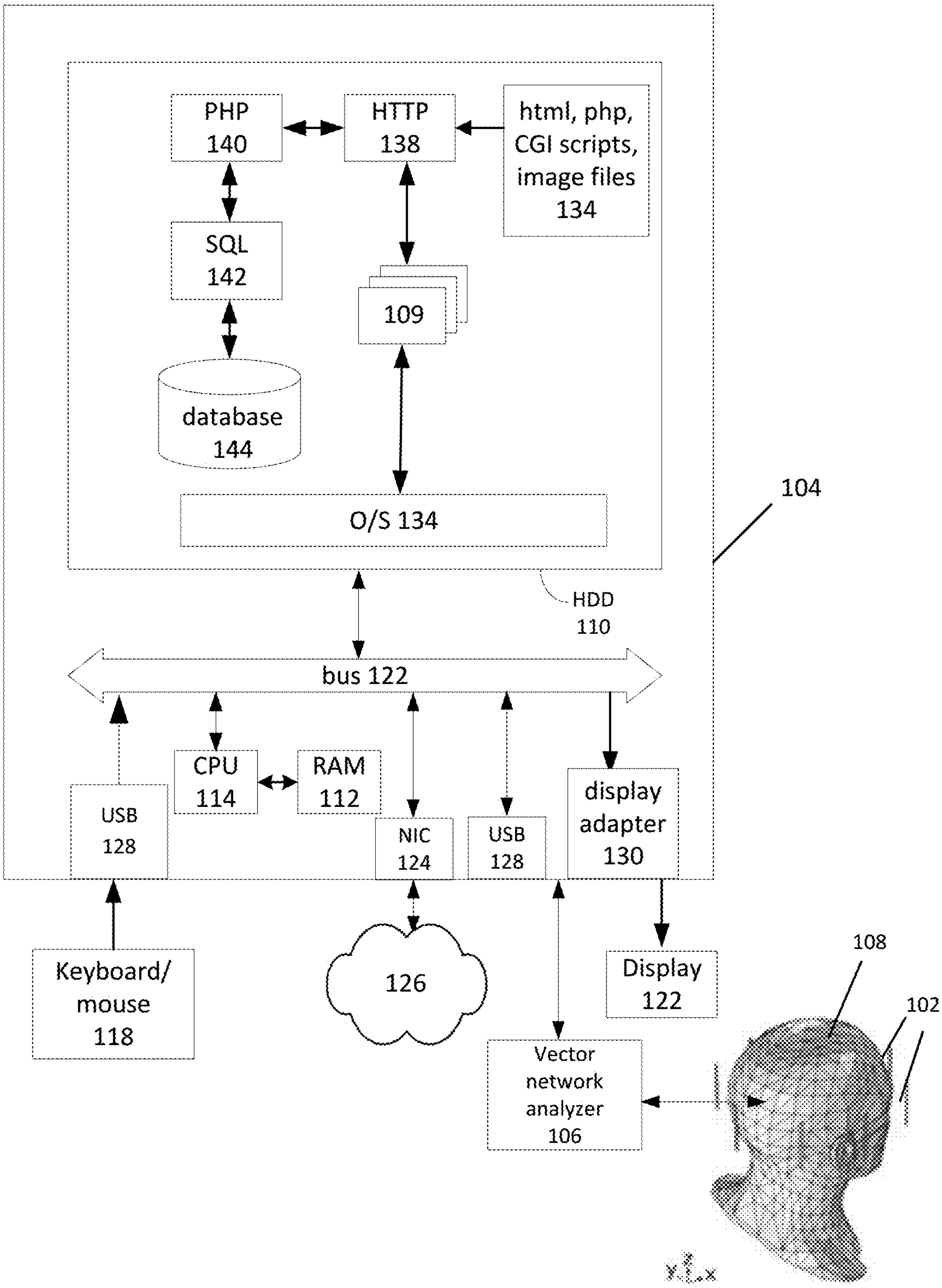
FIG. 1 is a block diagram of an apparatus for medical sensing in accordance with an embodiment of the present invention.

As shown in FIG. 1, a medical sensing apparatus includes an array of microwave antennas 102 coupled to a data processing component 104 via a vector network analyzer (VNA) or transceiver 106.

The array of microwave antennas 102 is arranged to receive the head 108 of a subject whose brain is to be sensed and/or imaged, as shown, so that each antenna of the array can be selectively energised to radiate electromagnetic waves or signals of microwave frequency into and through the subject's head 108 to be scattered, and the corresponding scattered signals detected by all of the antennas 102 of the array, including the antenna that transmitted the corresponding signal.

Figure 2:
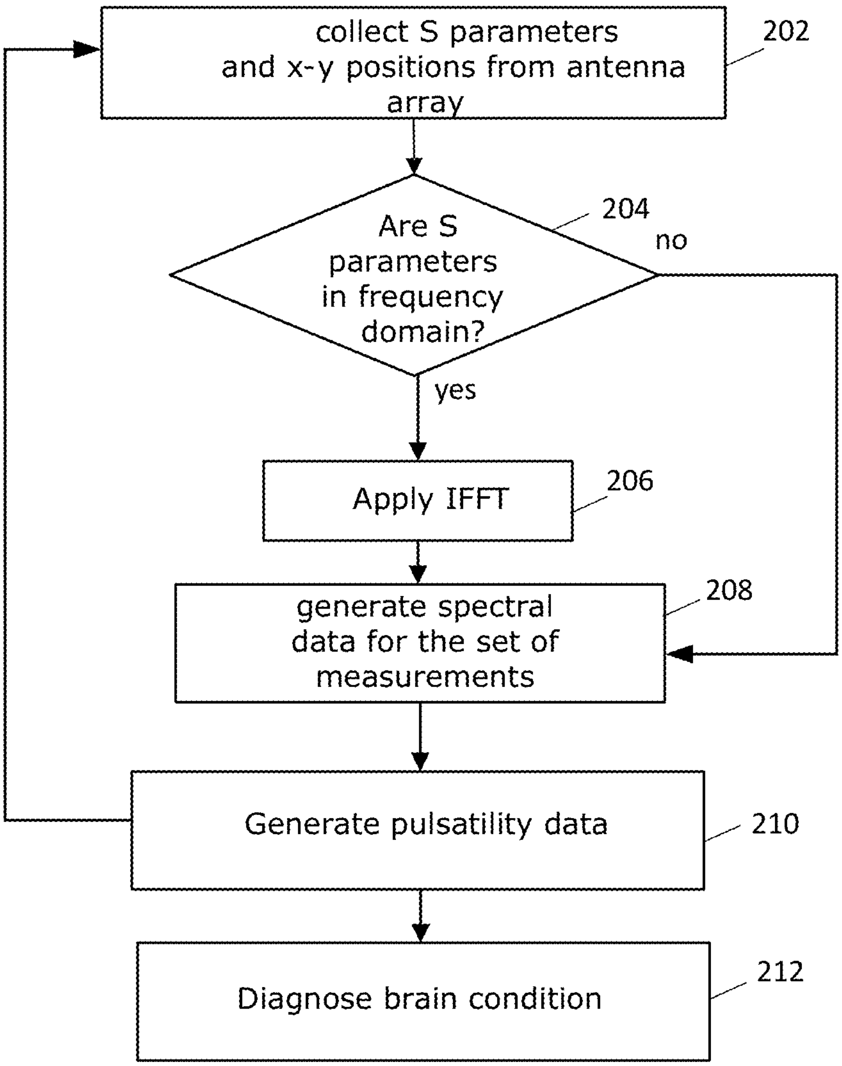
FIG. 2 is a flow diagram of a process for medical sensing in accordance with an embodiment of the present invention.

The vector network analyser (VNA) 106 energises the antennas as described above, and records the corresponding signals from the antennas as data (referred to herein as 'scattering' data) representing the amplitudes and phases of the scattered microwaves in a form that is known in the art as "scattering parameters" or "S-parameters". The VNA 106 sends this data to the data processing component which executes a medical sensing process, as shown in FIG. 2, to generate information on internal features of the imaged object (e.g., brain clots, bleeding sites, and other features) that can (but need not) be used to generate images of those features. In the described embodiments, a VNA that has a large dynamic range of more than 100 dB and a noise floor below −100 dBm is used to activate the antennas 102 to transmit electromagnetic signals across the frequency band of 0.5 to 4 GHz and receive the scattered signals from those antennas 102.

Although the data processing component 104 of the described embodiments is in the form of a computer, this need not be the case in other embodiments. As shown in FIG. 1, the data processing component 104 of the described embodiments is a 64-bit Intel Architecture computer system, and the medical sensing processes executed by the medical sensing apparatus are implemented as programming instructions of one or more medical sensing modules 109 (including an acquisition component, a spectral generation component, a pulsatility generation component, and in some embodiments a diagnosis component) stored on non-volatile (e.g., hard disk or solid-state drive) storage 110 of or associated with the computer system. However, it will be apparent that at least parts of the medical sensing processes could alternatively be implemented in one or more other forms, for example as configuration data of a field-programmable gate array (FPGA), or as one or more dedicated hardware components, such as application-specific integrated circuits (ASICs), or as any combination of such forms.

The data processing component 104 includes random access memory (RAM) 112, at least one processor 114, and external interfaces 116, 118, 120, all interconnected by a bus 122. The external interfaces include a network interface connector (NIC) 124 which connects the medical sensing apparatus to a communications network such as the Internet 126, and universal serial bus (USB) interfaces 128, at least one of which may be connected to a keyboard 118 and a pointing device such as a mouse 118, and a display adapter 130, which may be connected to a display device such as an LCD panel display 132.

The data processing component 104 also includes an operating system 134 such as Linux or Microsoft Windows, and in some embodiments includes additional software modules 138 to 142, including web server software 138 such as Apache, available at http://www.apache.org, scripting language support 140 such as PHP, available at http://www.php.net, or Microsoft ASP, and structured query language (SQL) support 142 such as MySQL, available from http://www.mysql.com, which allows data to be stored in, and retrieved from, an SQL database 144.

Together, the web server 138, scripting language module 140, and SQL module 142 provide the medical sensing apparatus with the general ability to allow remote users with standard computing devices equipped with standard web browser software to access the medical sensing apparatus and in particular to determine (and typically view a visual representation of) the location(s) of a stroke or other form of brain anomaly or injury, and optionally to monitor its progress over time.

For the sake of simplicity, the medical sensing apparatus and process are described herein in the context of a single array of antennas lying in a plane that passes through the subject's brain and stroke region (i.e., to provide 2D localisation of the stroke), although the same steps apply to "3D" cases in which there are two or more layers of antennas available to provide three-dimensional localization.

As shown in FIG. 2, the medical sensing process begins with the acquisition component accessing (e.g., receiving from the VNA 101) or otherwise accessing (e.g., from storage) at step 202 scattering data in the form of a set of "S-parameters" representing at least a two-dimensional array of measurements of electromagnetic wave scattering by internal features of a subject's brain, as described above, for a corresponding measurement time. In the described embodiments, an array of 16 antennas 105 is used, resulting in a 16×16 array or matrix of measurements in either the frequency domain or the time domain.

At step 204, a test is performed to determine whether the S-parameters are in the frequency domain, and, if so, then at step 206 an Inverse Fast Fourier transform ("IFFT") is applied to the S-parameters individually to convert them to the time domain.

At step 208, the spectral generation component processes the time domain scattering parameters to identify the temporal location of the subject's skull in the measured signals, this being indicated by a large discontinuity in the time domain response. Once the discontinuity has been identified, then only the portion of each signal after the discontinuity, these being signals from within the subject's skull, are processed further. Specifically, the remaining portion of each signal is processed to generate spectral data representing, for each antenna, a corresponding frequency spectrum representing measured intensity as a function of frequency at that measurement time. In the described embodiments, this is achieved using a fast Fourier transform ("FFT").

Steps 202 to 208 are repeated for successive and regularly spaced measurement times to accumulate, for each antenna, a two-dimensional array of data representing the corresponding spectral data for that antenna as a function of measurement time. In the described embodiments, the measurements are repeated at a measurement frequency of at least 30 Hz, so that successive measurements are spaced apart by a period of about 0.03 seconds or less. However, a measurement repetition frequency as low at 10 Hz can be used in other embodiments.

By repeating steps 202 to 208 at frequencies greater than patient's pulse rate, the process is able to image or otherwise detect changes in the volume of blood in different regions of the patient brain over time, and in particular with each heartbeat. Moreover, where blood flow in a region of the brain is affected by an anomaly such as stroke, such a region can imaged or otherwise detected by contrast with the normal blood volume changes in adjacent or surrounding regions of the brain with each heartbeat. It will be appreciated that the process can be performed in real time, to image or otherwise detect dynamic blood flow in a patient in real-time, or at a later time after the electromagnetic scattering measurements have been made. In any case, such dynamic measurements are also referred to herein as 'pulsatility' measurements or signals or data.

At step 210, the spectral data as a function of time is processed by the pulsatility generation component to generate, for each antenna, corresponding pulsatility data representing blood pulsations of the corresponding region of the subject's brain. In the described embodiment, the processing applies a form of transform known to those skilled in the art as a "short time Fourier transform" ("STFT") to respective portions of the signal corresponding to respective regions within the subject's skull, as described above. Thus the STFT involves separating the time domain signal into overlapping windows (with a windowing function), which are converted to the frequency domain using a fast Fourier transform. However, in an alternative embodiment, a user of the apparatus can select a depth of interest within the subject's head, and the STFT is applied to signals corresponding to that selected depth.

As there are notable differences in intra-cranial pulsations between ischemic stroke patients and healthy volunteers, the measured pulsations can be used (by the diagnosis component of the medical sensing modules 109) to diagnose ischemic stroke, and to identify its approximate location within the subject's brain. Moreover, changes in brain pulsations are also markers of several other diseases, including traumatic brain injury, and hydrocephalus, for example.

Figure 3A:
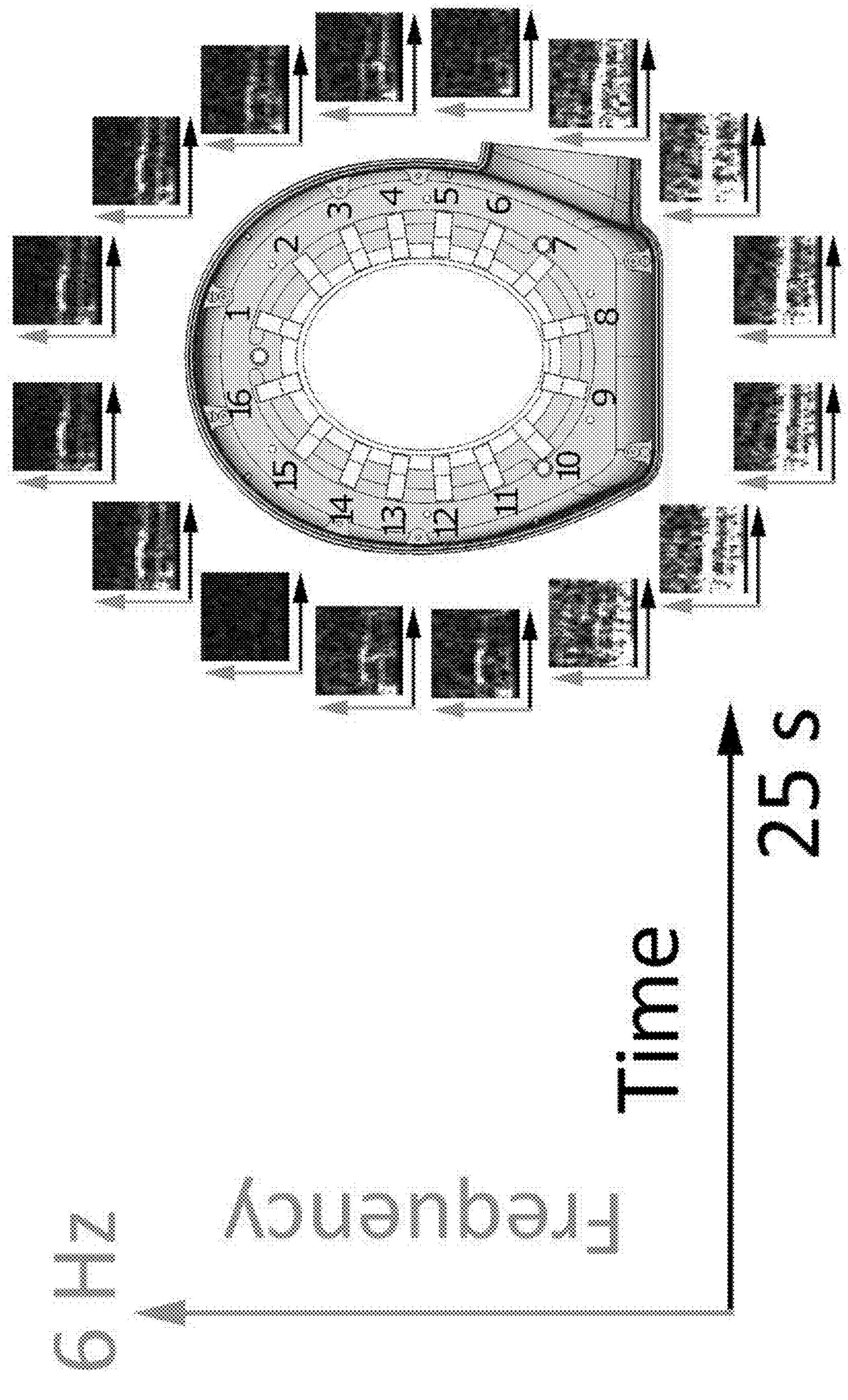
FIGS. 3 (*a*) and (*b*) illustrate spectral data generated by the process of FIG. 2 for each antenna as a function of time for two participants, respectively.
Figure 3B:
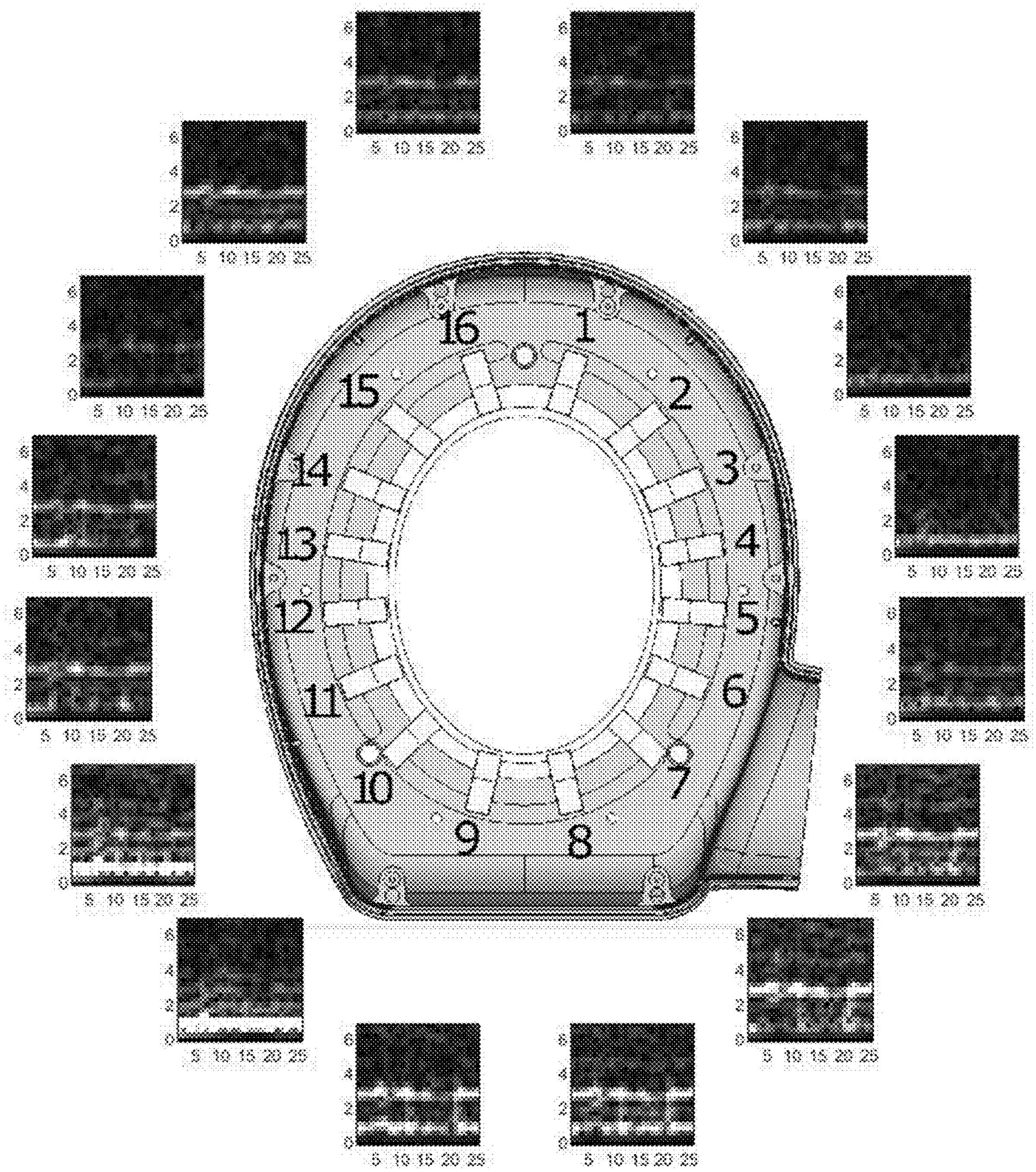
Figure 3C:
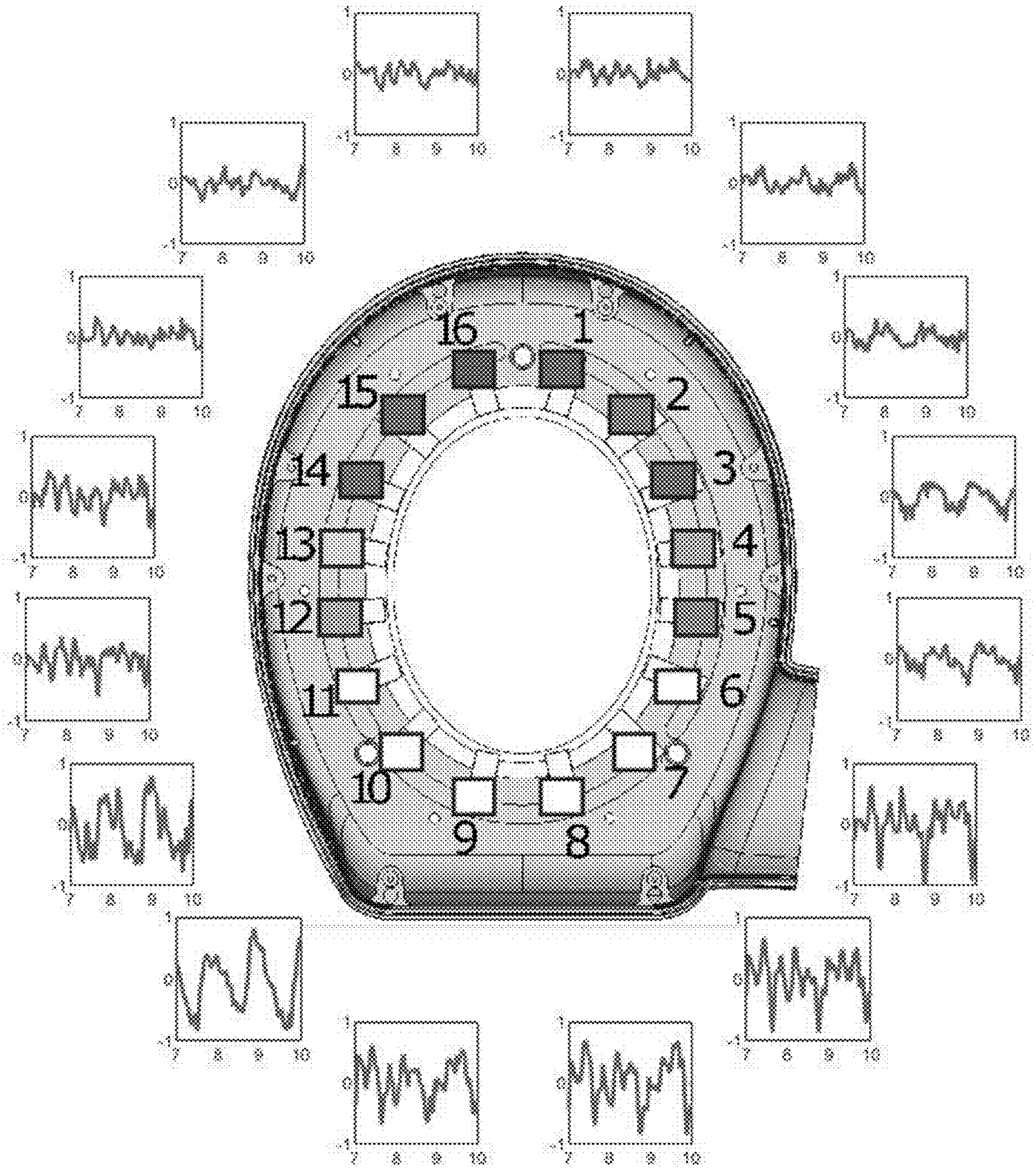

The ability of the process to measure blood pulsations within the human brain is demonstrated in FIG. 3. FIG. 3 (*a*) is a schematic plan view of the antenna array, including 16 separate antennas. Superimposed on this view are, for each antenna, corresponding two-dimensional plots representing measured intensity as a function of time (horizontal axis) and frequency (vertical axis), using the short time Fourier transform (STFT).

FIG. 3 (*b*) is the same as FIG. 3 (*a*), but for a second subject, and FIG. 3 (*c*) shows the corresponding pulsatility signals for the second subject generated from the spectral data. Additionally, each of the antennas is colour-coded to indicate the average power of the signal during each measurement time period. When this average power is higher at an antenna than at the other antennas, it indicates that the head is closer to that particular antenna.

Figure 4:
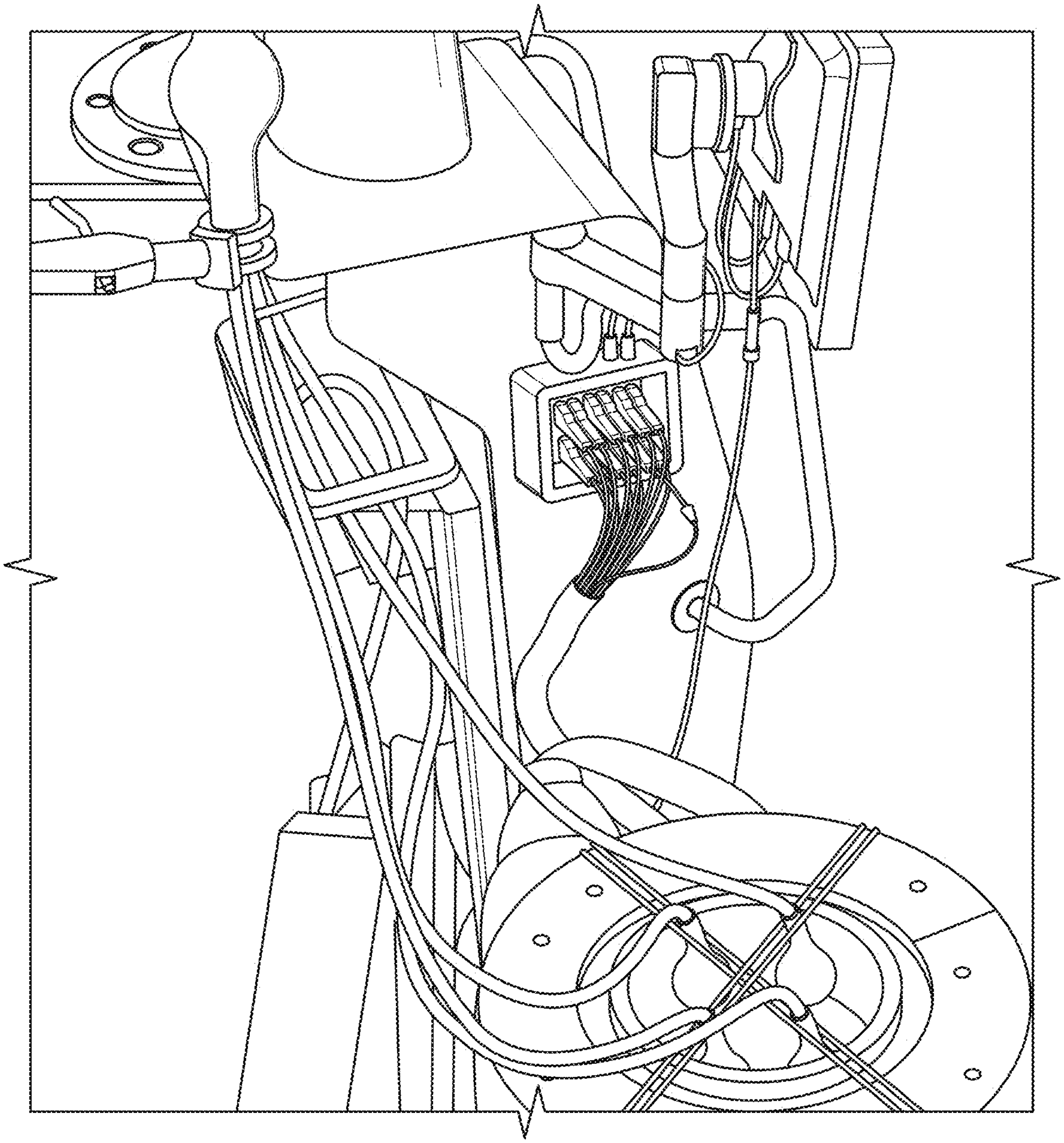
FIG. 4 is a photograph of a phantom instructed by the inventors to demonstrate the effectiveness of the process and apparatus in detecting pulse anomalies.

To demonstrate the ability of the described apparatus and process to detect changes in pulse, a human head phantom was constructed, using a solid two layered shell to emulate the properties of the skin and skull, and a fluid emulating the average head properties inside, as shown in FIG. 4. Additionally, four hollow bulbs composed of a resilient material through which a blood-emulating fluid was pumped were placed inside.

Figure 5:
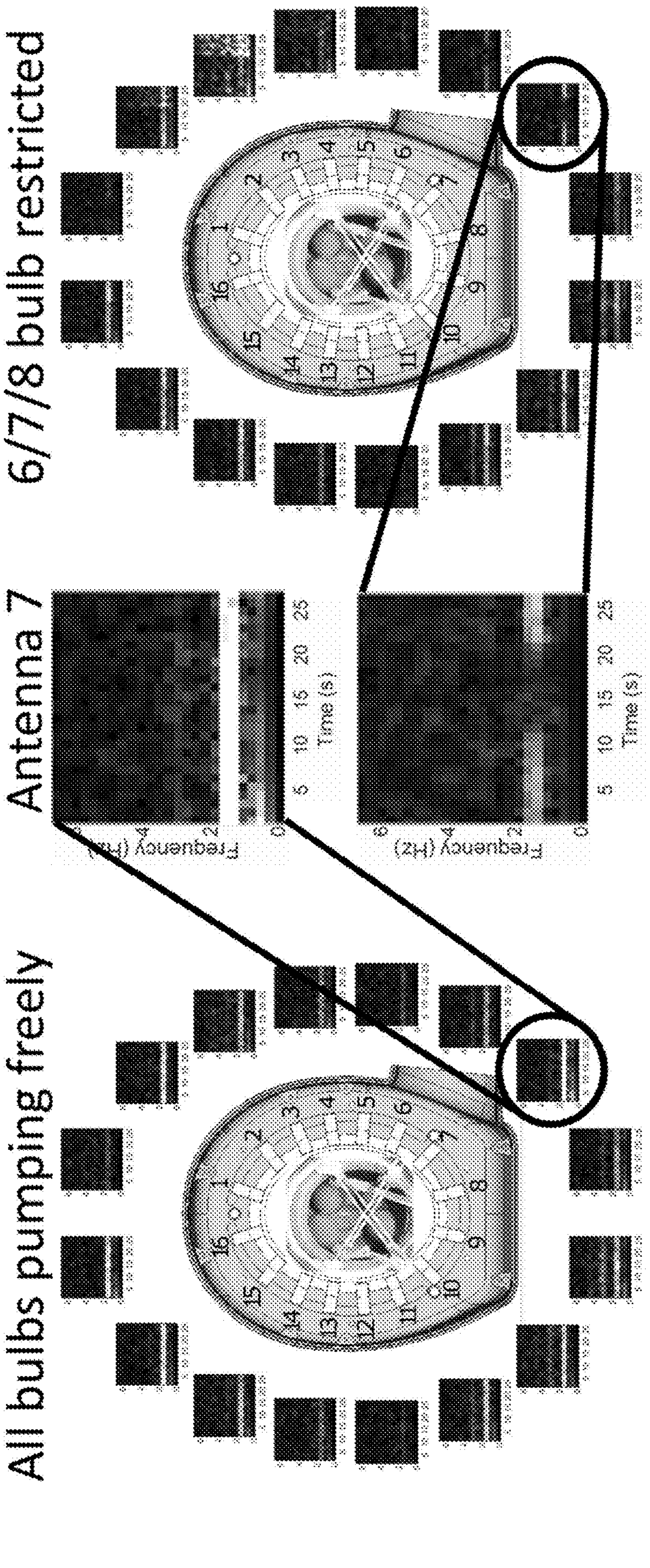
FIG. 5 illustrates the changes in the spectral data of an antenna corresponding to a region of brain tissues subject to pulse restriction.

The left-hand side of FIG. 5 shows a plan view image of the phantom located within the antenna array, and superimposed spectral data for each antenna. The right-hand side of FIG. 5 shows the same thing, but where fluid flow through one of the four bulbs (located near the antennas numbered 6, 7 and 8) was deliberately restricted. The central part of FIG. 5 shows the corresponding spectral data from antenna 7. Comparison of the spectral data from the unrestricted (upper plot) and restricted (lower plot) phantom confirms that the presence of the restriction can easily be detected from the spectral data. In a living patient, such changes in the spectral data can be used to detect the presence of brain disease, as described above, and its approximate location corresponding to the location of the corresponding antenna. Using an array of 16 antennas, these results show that a loss of pulse can be located within the head to an accuracy of approximately ⅛ of the head dimensions.

Once such an anomaly has been detected, its location can be indicated by superimposing a corresponding image of the region of the anomaly onto an image of the subject's brain, generated using any suitable microwave imaging process known to those skilled in the art, or an imaging process such as described in the applicant's prior patent applications.

Many modifications will be apparent to those skilled in the art without departing from the scope of the present invention.

The invention claimed is:

1. A computer-implemented process for medical sensing, the process including the steps of:

accessing scattering data representing successive sets of measurements of electromagnetic wave scattering by internal features of a body part of a living subject, each said measurement representing scattering of electromagnetic waves emitted by a corresponding antenna of an array of antennas disposed about the body part as measured by a corresponding antenna of the array of antennas at a corresponding time, wherein the successive sets of measurements are temporally spaced apart, and wherein the scattering data comprises scattering parameters (S-parameters) acquired by a vector network analyzer (VNA);

processing each of the measurements to generate corresponding spectral data representing intensities measured by the corresponding antenna at the corresponding time as a function of frequency, wherein said processing includes, when the measurements are S-parameters in the frequency domain, applying an Inverse Fast Fourier transform (IFFT) to convert the S-parameters to the time domain; and processing the spectral data of each antenna for successive times to generate corresponding pulsatility data representing successive blood pulsations within a corresponding spatially localized region within the body part.

2. The process of claim 1, wherein the temporal spacing between successive measurements of each antenna is about 0.03 seconds or less.

3. The process of claim 1, wherein the body part is the subject's head, and the pulsatility data represents blood pulsations within a corresponding spatially localized region within the subject's brain.

4. The process of claim 3, including processing the pulsatility data of each antenna to diagnose a brain condition of the subject.

5. The process of claim 4, wherein the brain condition is a brain condition selected from: haemorrhagic stroke, ischemic stroke, traumatic brain injury, and hydrocephalus.

6. The process of claim 1, wherein said processing includes processing time domain signals representing the measurements of electromagnetic wave scattering to select a portion of each time domain signal corresponding to scattering within the body part, and processing the selected portions of the time domain signals to generate the spectral data.

7. An apparatus for medical sensing, the apparatus including at least one processor configured to execute the process of claim 1.

8. A computer-readable storage medium having stored thereon executable instructions that, when executed by at least one processor of a data processing apparatus, cause the apparatus to execute the process of claim 1.

9. An apparatus for medical sensing, including:

an acquisition component configured to access scattering data representing successive sets of measurements of electromagnetic wave scattering by internal features of a body part of a living subject, each said measurement representing scattering of electromagnetic waves emitted by a corresponding antenna of an array of antennas disposed about the body part as measured by a corresponding antenna of the array of antennas at a corresponding time, wherein the successive sets of measurements are temporally spaced apart, and wherein the scattering data comprises scattering parameters (S-parameters) acquired by a vector network analyzer (VNA);

a spectral generation component configured to process each of the measurements to generate corresponding spectral data representing intensities measured by the corresponding antenna at the corresponding time as a function of frequency, wherein said processing by the spectral generation component includes, when the measurements are S-parameters in the frequency domain, applying an Inverse Fast Fourier transform (IFFT) to convert the S-parameters to the time domain; and a pulsatility generation component configured to process the spectral data of each antenna for successive times to generate corresponding pulsatility data representing successive blood pulsations within a corresponding spatially localized region within the body part.

10. The apparatus of claim 9, wherein the temporal spacing between successive measurements of each antenna is about 0.03 seconds or less.

11. The apparatus of claim 9, wherein the body part is the subject's head, and the pulsatility data represents blood pulsations within a corresponding spatially localized region within the subject's brain.

12. The apparatus of claim 11, including a diagnosis component configured to process the pulsatility data of each antenna to diagnose a brain condition of the subject.

13. The apparatus of claim 12, wherein the brain condition is a brain condition selected from: haemorrhagic stroke, ischemic stroke, traumatic brain injury, and hydrocephalus.

14. The apparatus of claim 11, wherein the spectral generation component is configured to process time domain signals representing the measurements of electromagnetic wave scattering to select a portion of each time domain signal corresponding to scattering within the body part, and to process the selected portions of the time domain signals to generate the spectral data.

* * * * *